(12) United States Patent
Martikka et al.

(10) Patent No.: US 7,764,990 B2
(45) Date of Patent: Jul. 27, 2010

(54) METHOD AND DEVICE FOR MEASURING EXERCISE LEVEL DURING EXERCISE AND FOR MEASURING FATIGUE

(75) Inventors: Mikko Martikka, Vantaa (FI); Veikko Koivumaa, Espoo (FI); Pekka Tolvanen, Kuopio (FI)

(73) Assignees: Suunto Oy, Vantaa (FI); Mega Elekroniikka Oy, Kuopio (FI)

( * ) Notice: Subject to any disclaimer, the term of this patent is extended or adjusted under 35 U.S.C. 154(b) by 904 days.

(21) Appl. No.: 11/173,773

(22) Filed: Jun. 30, 2005

(65) Prior Publication Data

US 2006/0079800 A1   Apr. 13, 2006

Related U.S. Application Data

(60) Provisional application No. 60/585,106, filed on Jul. 1, 2004.

(51) Int. Cl.
*A61B 5/0488* (2006.01)
(52) U.S. Cl. .......................... 600/546; 607/48; 600/520
(58) Field of Classification Search ................ 514/546; 600/520, 546, 587, 300; 700/91–93; 607/48
See application file for complete search history.

(56) References Cited

U.S. PATENT DOCUMENTS

| | | | | |
|---|---|---|---|---|
| 5,067,710 A | * | 11/1991 | Watterson et al. | 482/3 |
| 5,361,775 A | * | 11/1994 | Remes et al. | 600/546 |
| 5,474,083 A | * | 12/1995 | Church et al. | 600/546 |
| 5,752,521 A | * | 5/1998 | Dardik | 600/520 |
| 6,006,129 A | * | 12/1999 | Watson | 600/546 |
| 6,143,784 A | * | 11/2000 | Greenhaff et al. | 514/546 |
| 6,185,451 B1 | * | 2/2001 | Richardson et al. | 600/546 |
| 6,411,841 B2 | | 6/2002 | Heikkila | 600/513 |
| 6,673,026 B2 | * | 1/2004 | Pozos et al. | 600/587 |
| 6,790,178 B1 | * | 9/2004 | Mault et al. | 600/300 |
| 2001/0049482 A1 | * | 12/2001 | Pozos et al. | 600/587 |

OTHER PUBLICATIONS

Jammes, Yves et al. "Correlation between Surface Electrogram, Oxygen Uptake and Blood Lactate Concentration during Dynamic Leg Exercises." Respiration Physiology 112 (1998) 167-174.*
Chwalbinska-Moneta et al., "Relationship Between EMG Blood Lactate, and Plama Catecholamine Thresholds During Graded Exercise in Men." Journal of Physiology and Pharmacology (1998) 49, 3, 433-441.*

* cited by examiner

*Primary Examiner*—Carl H Layno
*Assistant Examiner*—Luther G Behringer
(74) *Attorney, Agent, or Firm*—Harrington & Smith

(57) ABSTRACT

A method for measuring exercise level during exercise and for measuring fatigue, in which method electrical signals produced by active muscles are measured with a measuring device and feedback is given from an exercise with a perceivable signal from a feedback device. A device for measuring exercise level and fatigue during exercise, which device includes sensors for measuring electrical signals from active muscles and a feedback device for giving feedback. A momentary exercise level and the level of fatigue of a person are measured or estimated by measuring besides electrical signals received from muscles also other quantities describing exercise and from measuring results one or several indexes are calculated by means of which exercises carried out at different times and under different circumstances are comparable with each other.

16 Claims, 1 Drawing Sheet

Figure 1:
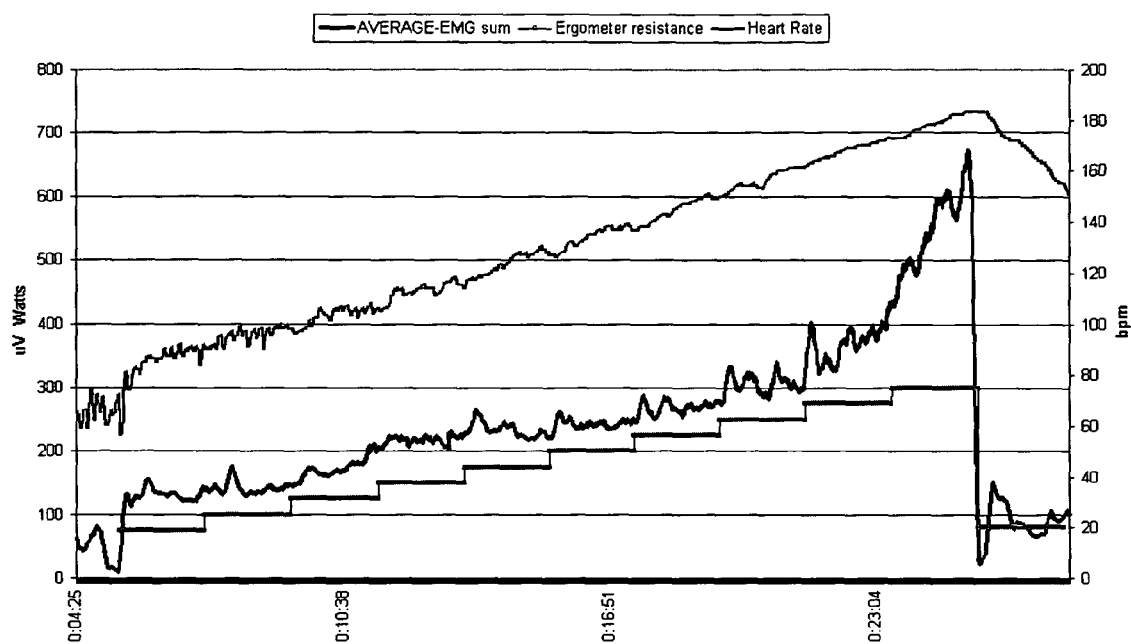

METHOD AND DEVICE FOR MEASURING EXERCISE LEVEL DURING EXERCISE AND FOR MEASURING FATIGUE

CROSS REFERENCE TO RELATED APPLICATION

This application claims priority to U.S. Provisional Application Ser. No. 60/585,106 filed on Jul. 1, 2004.

The present invention relates to a method for measuring exercise level during exercise and for measuring fatigue, in which method electrical signals produced by active muscles are measured with a measuring device and feedback is given from the exercise with a perceivable signal from a feedback device. In addition, the invention relates to a device for applying the method, which device comprises sensors for measuring electrical signals from active muscles and a feedback device for giving feedback.

It is commonly known that by means of an EMG-signal received from muscles it is possible to measure levels of activity of muscles and that from those it is possible to calculate various quantities describing the functioning of muscles and the body. EMG-signal is usually measured through electrodes placed on the skin overlying muscles. These electrodes are placed and fastened on a muscle with some suitable fastening means such as glue in the electrode itself, with a tape, belt etc. Measured EMG-signals are typically transmitted either to be presented in real-time on a display device or signals are stored in file format for later examination and analyses.

EMG-signal is typically measured in two different ways depending on what kind of measuring accuracy or analysis of results is desired or, on the other hand, what kind the processing capacity of the device is. The most versatile measuring and analyzing alternatives are obtained by measuring EMG bipolar as so-called RAW EMG-signal. By using high enough sampling frequency, e.g. 1000-10000 Hz, it is possible to make analyses from a signal competent to scientific research accuracy by means of e.g. FFT spectrum calculation. Measuring of a RAW-signal requires a great processing capacity and memory capacity from the device. Another typical EMG measuring method is so-called averaged i.e. AVERAGE-EMG method, in which an EMG-signal received from a muscle is first rectified and after that averaged sliding across chosen averaging time e.g. 0.1-1 sec. By analyzing an AVERAGE-EMG-signal typically loading of muscles is estimated, loading comparisons are made, activation velocity and times of muscles are examined etc. Measuring of an AVERAGE-EMG-signal is in principle possible to carry out by a very simple device.

Each EMG-signal forms a so-called profile, in which active and passive phases of a measured muscle are visible as amplitude changes of the signal. In addition, the frequency spectrum of a signal includes information on the functioning of a muscle. Quantities describing the functioning of a muscle are e.g.:

muscle load and changes in it
distribution of load on different muscles of the body
side difference between two symmetrical muscles when loaded simultaneously with similar load
the activation order, activation times, reaction velocity of muscles etc.
comparison of activation profiles of muscles in various phases of an exercise and on different test subjects
fatigue of muscles In addition, from the shape of an EMG-signal, amplitude, frequency spectrum and changes in those, it is possible to calculate a great number of other quantities to be followed and monitored.

Furthermore, it is commonly known that from an electrical so-called ECG-signal of the heart, it is possible to identify separate heartbeats and that from those it is possible to calculate various quantities describing the functioning of the heart. ECG-signal is usually measured through electrodes placed on the skin in various placed on the body. Quantities describing the functioning of the heart are e.g.:

number of heartbeats/minute i.e. heart rate
time difference between two heartbeats and its changes i.e. R-R interval
total number of heartbeats during a given exercise/period i.e. number of R-R intervals In addition, from the shape, amplitude and changes in normal rhythm (arrhythmias) of the heart quantities to be followed and monitored may be calculated.

Furthermore, it is commonly known that biomechanical movements may be measured by inertia sensors. For example, acceleration, gyro and magnetic sensors are inertia sensors. Acceleration sensors give a signal proportional to acceleration of movement in given direction. Gyro sensors give a signal proportional to angular velocity of movement. Magnetic sensors may be used for detecting static position as well as detecting the direction of movement. In devices, one, two or three directions may be utilized.

Furthermore, it is commonly known that changes in terrain may be monitored by means of an altitude and/or tilt sensors. It is also possible to monitor the distance moved, speed and changes in the altitude of terrain with GPS.

It is common to monitor the active functioning of the heart and muscles and simultaneously give feedback of their functioning in various ways such as visual numbers, graphics or by means of sound. The feedback device is located in the measuring device itself or in a separate display device at a short distance from it. A typical example of feedback devices are so-called heart rate monitors, which include a separate heart rate band to be placed on the chest and a display device to be fastened on the wrist, which device may have an integrated altitude sensor in it. Frequently these measuring and display devices are, however, a part of a larger system, in which case training and exercising must be carried out in certain place such as an exercise research laboratory.

Devices available for measuring of muscle load are mainly meant for research use i.e. measurements may be made only at carefully chosen time, under controlled circumstances and under guidance of a skilled person. Besides a measuring device most often also a separate computer and a programme are needed, by means of which measuring methods interesting to the user are first programmed to the device and on the other hand, results may be received only by an after analysis of the data gathered in the memory of the device. The mentioned devices are not suitable for personal and every day use because they should be light, easy to use, advantageous and the transmission of information between the parts of the device should happen wirelessly.

Present measuring methods of body load applicable for every day use are based on monitoring the heart rate and changes in it. When the load is steady or changes in it are slow the heart rate is a good indicator of the load level but in all exercise performances mere monitoring of the heart rate is not enough for estimating of the optimal load and especially the distribution of load. During exertion, the heart reacts mostly through changes in oxygen need to all changes in the body but it does not identify the parts where the load changes take place. The heart is also not capable of noticing fast changes in load, which, however, may have impact e.g. on performance level, endurance, fatigue of muscles or on generating of substances indicating stiffening e.g. lactate and such on the exercise itself. In addition, at least on low levels of heart rate besides the physical load also mental factors affect the heart rate, in which case the reliability of results as indicator of physical load suffers. External factors such as rises and falls in terrain, contrary wind etc. as well as momentary changes in running rhythm may cause unnecessary and premature fatigue in leg muscles, which might be prevented by reacting fast to the changed load e.g. by slowing the speed or by changing the running style. By measuring the most important muscle groups used in running and their load this kind of real-time monitoring and anticipating is possible.

Training of exercise level and endurance of muscles requires intentional loading of muscles on various power levels depending on what section of exercise level is desired to be developed. For rising basic endurance, aerobic longterm exertion under light load is needed. On the other hand, the purpose of so-called lactate exercises is to develop extreme exertion tolerance, in which case maximum loading levels are necessary. In addition, depending on various sports and targets intermediate levels of earlier mentioned loads are needed.

Load is measured by current methods used in laboratories by monitoring muscle functioning muscle by muscle and thus the exercise capacity of a person is tried to be estimated. EMG measuring of one muscle describes the functioning of the muscle in question precisely but results from that may not be generalized to describe the total exertion of the limb in question or the whole part of the body. Therefore, measurements must be made simultaneously from several muscles affecting movements of the limb and summing the results the total load may be estimated. In present devices this means increasing of the number of measuring channels and therefore more complicated and unpractical construction.

By present methods, information about a training or exercise performance is received during training/exercising but the problem is in presenting the information and/or feedback continuously and wherever in performance place regardless of circumstances and/or location. In addition, in many sports, real-time information about muscles of the body and/or limbs and their functioning is needed and with present devices this kind of information is not received.

It is commonly known that the performance level and the level of fatigue of a muscle may be estimated by measuring and analyzing an EMG-signal produced by the muscle. This kind of method has been described e.g. in U.S. Pat. No. 5,361,775 of Mega Electronics Ltd, in which patent with a FFT i.e. spectrum analysis made from an EMG-signal it is possible to reveal several quantities correlating with fatigue of a muscle. Fatigue of a muscle can be seen e.g. as lowering of mean frequency in power spectrum of an EMG-signal and on the other hand as rising of averaged EMG level of activity. The method has been confirmed functionable when fatigue of a muscle is measured during static load. FFT calculation gives indicative results also during a dynamic exercise but continuously alternating muscle contractions as well as interferences due to motion change the frequency content of an EMG-signal such that the results obtained by FFT calculation are not as precise and reliable as in static measuring. FFT calculation made from dynamic motion may be specified by utilizing motion sensors fastened to the person examined during the test, by means of which sensors interferences generated in the signal may be eliminated or limit the areas to be taken into account in FFT calculation advantageous in terms of calculation.

It is also known that fatigue of the body may be measured by means of parametres connected to the heart rate level and breathing. Usually, so-called aerobic and anaerobic threshold level is tried to be identified because they are the easiest to be noticed and they have a connection to fatigue level of the body. One method of this kind has been described in U.S. Pat. No. 6,411,841 B2 of Polar Electro Oy in which e.g. from changes in heat rate level the lactate content of the body is estimated, which content describes fatigue of the body. Another method to notice the anaerobic threshold is so-called Conconi method, in which momentary flattening occurring in heart rate level is examined by the threshold level in question. A common way of measuring lactate content of blood is based on a blood sample taken from a fingertip or earflap, which is then analyzed in a separate measuring device.

With present portable measuring methods of exercise, mostly heart rate monitors, it is possible to estimate the level of fatigue of a person but they are not capable of identifying in which part of the body fatigue is occurring and the influence of fatigue on the performance itself is not possible to be predicted during the exercise. From a heart rate signal measured with a heart rate monitor it is possible by means of a heart rate variability analysis to calculate and estimate various things such as exertion level of the exercise, recovering velocity, maximum oxygen uptake capacity etc.

When using changes in heart rate in measuring of the lactate level and when measuring from EMG-signal the exercise level and fatigue of muscles by means of FFT analysis the measuring event must be carried out with a standard testing system, which is usually possible only in a research laboratory designed for the purpose. In addition, for generating fatigue external either gradually or evenly growing load is needed to which the level of fatigue may be proportioned. In case the exertion caused by an exercise varied the whole time sporadically, it would be difficult to detect from changes in EMG-signal which changes are caused by changes of load due to external factors and which are caused by real fatigue of a muscle.

The objective of the invention is to provide a method and a device, with which it is possible to measure and monitor exercise level and fatigue during exercise in real-time, fast and reliably. Especially the objective of the invention is to provide a method and a device, with which it is possible to monitor the level of fatigue and to predict fatigue. Furthermore, the objective of the invention is to provide a device, which is relatively light, easy to use, advantageous and suitable for every day use.

The objective of the invention is accomplished by a method and device, the characteristics of which are presented in the claims.

In the method in accordance with the invention a momentary exercise level and the level of fatigue of a person are calculated or estimated by measuring besides electrical signals received from muscles also other quantities describing exercise and from measuring results one or several indexes are calculated by means of which exercises carried out at different times and under different circumstances are comparable with each other and by means of which the person may immediately monitor and optimize his/her exercise and/or after exercise analyze his/her performance. Analyses made from signals are presented to the user by means of representation methods easy to comprehend such as numeric values or while necessary also by means of illustrative graphic diagrams. The person may easily and fast monitor his/her exercise and level of fatigue through the entire exercise in realtime or he/she may analyze the performance after the exercise versatile.

In an advantageous application of the invention, also other biosignals and/or movements of a person are measured. This information is taken into account and by means of it the exercise and the level of fatigue may better be estimated.

In the next advantageous application of the invention, the progression velocity of a person is measured. The progression velocity affects the exercise and the level of fatigue of a person and such monitoring, measuring and taking into account of it improves the accuracy of measuring.

In the next advantageous additional application of the invention, external circumstances are measured. External circumstances such as terrain, the weather, condition of the ground surface also affect the exercise and monitoring, measuring and taking into account of them improves the accuracy of measuring.

In the next advantageous additional application of the invention, the resistance caused by an exercise means is measured. An exercise means affects a performance and the resistance it causes, among other things, may be calculated and taken into account in analyzing the exercise. This improves the estimation and comparisons may be made between exercises with different kinds of exercise means.

In the method in accordance with the invention signals, measured from the functioning of active muscles of the body and the heart and electrical signals, received from motion sensors placed on the body or on various parts of the body such as on an outfit or similar, are combined in a suitable way and exercise level and the level of fatigue of a person are estimated from those. In addition, other quantities describing exercise such as the progression velocity, external circumstances and resistance due to an exercise means may be combined to the earlier mentioned signals.

With the method in accordance with the invention, it is possible to measure and monitor the exercise level and fatigue of the body and especially different parts of the body as well as to give feedback from those during an exercise fast, reliably and simply. The method is based on combining and analyzing of quantities, received from muscle activities of muscles used in exercise and describing the functioning of the heart and the information created by the mechanical movements due to an exercise as well as advantageously external factors changing the exertion of an exercise in a way which is described later in this specification. In the method also changes caused by fatigue in biomechanical movements and motion paths of the body or a limb are utilized. In addition, in estimating fatigue changes caused by external variables such as altitude and steepness of terrain, the weather, wind and ground surface conditions or increasing or decreasing motion resistance of the exercise means may be taken into account. By means of the method a trainee receives immediate feedback with a noticeable signal or similar of the exercise, the functioning of the heart and muscles, balance and changes in balance of muscles, level of fatigue and changes in it, by means of which the trainee may adjust and improve the efficiency and profitability of an exercise as well as prevent weakening of exercise capacity due to fatigue of muscles. In this way he/she is able to estimate the level of exertion suitable for each situation and exercise target and predict the level of fatigue at the end of the exercise and thus adjust the effect of changes e.g. in terrain and circumstances to the result of the performance. For applying of the method typically an outfit is required but the necessary measurements may also be made by means of other sensors and accessories being placed on the body.

By combining information on the motion velocity of the body and/or parts of the body received by motion sensors it is possible to further define more closely the estimation of fatigue. As a special case for running and walking, there are devices on the market, which measure the progression velocity of a runner/walker. By combining EMG, the heart rate and velocity data taking the shape of terrain into account it is possible to see when e.g. the chosen basic velocity is heavier to maintain i.e. by the same work velocity reduces.

Identifying fatigue during dynamic and voluntary motion from an EMG-signal may be visualized by proportioning EMG activity to the changed load directed to the body or to a part of it, for example, when steepness of terrain, progression of velocity, rolling or sliding resistance etc. change. When exercise is carried out in equipment including sensors measuring mechanical strength, motion or some other similar quantities, e.g. in an ergometer or gym equipment, EMG levels of activation may be proportioned to these measuring results given by the equipment. These quantities are e.g. output power, intensity, torque, angular velocity, accelerations etc. In this case, by changing exercise techniques, position or other factors it is possible to search the less loading and less tiring progression method.

Fatigue of the body and muscles is seen also in slowening of activating velocities of muscles and, for example, in cyclic motion such as running and cycling, in growing of full width at half the maximum (FWHM) of activation profiles. In other words, a fatigued muscle may be loaded during one cycle as much as in the beginning but the activation time of the muscle is longer and the activation maximum is lower than in the beginning of the exercise. This is the result of a muscle using so-called slow-twitch muscle fibres in a long-term exercise but while a muscle becomes fatigued it has to compensate the lower usability of the slow-twitch fibres activating also so-called fast-twitch muscle fibres. Therefore, in an EMG-profile of a fatigued muscle there are potentials from several different muscle fibres and so-called motor units, which are formed from those, which cause the difference in a profile shape.

In heart rate and muscle activation profiles there are also other features changing as a function of velocity, shape of terrain, wind and other external factors to be found. When proceeding at constant speed the load of the body increases in up-hill and decreases in down-hill, but on muscle level the changes in load are distributed differently e.g. for controlling the balance and due to finding a suitable proceeding style for the shape of terrain and contrary wind. For example, while running up-hill or down-hill the mutual loading proportions of the muscles of front part and the back part of the thigh change, as muscle power is needed in rising phase to push forwards but while running down muscle power is more needed also to braking. While running up-hill the activation level of peroneal muscles rises but the activation level of tibial muscles falls. In studies also other changes visible in EMG-profiles of muscles have been detected, which changes are based on mutual relations of activation of e.g. extensor/flexor muscles of a limb.

When a sports performance/exercise includes as an essential part a section, which repeats as similar e.g. circling a running track of 400 meters at the same speed several times in succession the exercise level and fatigue may be estimated by comparing muscle loads between different cycles.

Estimation of the level of fatigue made in different ways is specified with information received from the heart rate, changes in R-R intervals etc. By a heart rate variability analysis, it is possible to integrate the total exertion of the exercise during the exercise. By combining EMG, heart rate level and heart rate variability analyses it is possible to estimate more precisely also the exercise level, endurance and fatigue.

A typical target related to endurance exercise and sports is to make the performance in as short time as possible, it means that a person aims to optimize his/her progression velocity compared to the length of travel as advantageous as possible. During an exercise, there are various correlations between progression velocity and muscle load. A part of these correlations are similar to all individuals but also individual differences e.g. in the body or muscle type, in fitness level or exercise techniques affect correlations. For example, in running load on both the front and the back thighs increases as the speed increases but the rise of their loads is not equal. Typically, the load on back thighs grows more then the load on front thighs as the speed grows. On the other hand, as the maximum speed is near to be achieved the front thighs may be loaded faster than the back thighs in order to achieve the top speed.

In addition to earlier mentioned phenomena load of muscles is also affected by fatigue, which is generated when a muscle is forced to be under continuous load for a long period of time without recovering relaxing periods. A continuous cyclic load when a muscle has to contract and relax at fast intervals such that the average loading level stays a long time at a level higher than normal, causes fatigue of a muscle. In both cases, fatigue leads eventually to so-called exhaustion, when protective mechanisms in muscles interrupt the functioning of the muscle in order to prevent damages and slowen or even stop proceeding. In practise fatigue of a muscle means that a fatigued muscle has to recruit more motor units and motor units including fast-twitch muscle fibres than before fatigue. This may be detected from an EMG-signal e.g. as a rise of AVERAGE-EMG-level, although the external work of a muscle does not change.

Because of the earlier mentioned explanations for measuring of exercise capacity and fatigue of a person by means of EMG-signal received from muscle activities it is absolutely necessary to know in what kind of situation, under what kind of circumstances and in what kind of environment the exercise is carried out in order to be able to identify and separate the desired quantities in measurements. Measuring results received in this way are comparable with corresponding exercises carried out at different times and under different kind of circumstances. Exercises in question may be compared with each other in which case it is possible to see and measure from results e.g. improvement as a result of training in fitness level or in exercise techniques or, on the other hand, worsening of exercise capacity caused e.g. by injuring.

The level of fatigue is visible also in changing of mechanical motions of the body, for example, in running as changes in a signal measuring vertical acceleration of an acceleration sensor placed on pelvis area etc. External factors affecting the body load also change the level of an EMG-signal. In case only the level of an EMG-signal and changes in it are examined, the signal changes more than in even or in evenly growing load. In this kind of signal, it is difficult to identify nonlinear points caused by fatigue of a muscle. However, an EMG-signal may be normalized by means of external variables such that only the nonlinear points caused by fatigue may be distinguished. By combining information from all available sources, conclusions may be made more reliable and they may be made faster and even in real-time during an exercise in which case the user benefits from them most.

In an advantageous application of the invention from measuring results, an index is calculated to describe the economy of a person's exercise level and exercise techniques. In endurance sports the economy of an exercise usually means progression with as small energy consumption as possible in comparison with progression velocity. Momentary energy consumption may be estimated by means of the sum of AVERAGE-EMG-signals of main muscle groups used for the exercise in question. A simple economy index is obtained by calculating the relation between progression velocity and the earlier mentioned AVERAGE-EMG. An exercise is the more economical the bigger the earlier mentioned ratio is. The index may include depending on sports also other measuring quantities used in exercise. By monitoring the economy index an athlete may vary the load of his/her motions in training phase and thus seek the most suitable exercise techniques for a competition situation.

In an advantageous additional application of the invention from measuring results an index is calculated to describe the level of fatigue of a person. Fatigue and recovering from it related to exercise depend, among other things, on exercise manner and duration of the exercise. In an exercise of short duration and on a high load level e.g. in sprint muscles become fatigued fast but on the other hand recovering to normal state is relatively fast. In long-term exercise, e.g. marathon race, the exercise level of an athlete may remain unchanged even for several hours without fatigue hindering the exercise. Normally fatigue arises slowly as a result of exhaustion of energy recourses of the body and on the other hand recovering from fatigue may take even several days. However, even short rises in exertion level during exercise may cause a fast fatigue reaction, exhaustion, from which an athlete is not able to recover during the exercise. To eliminate this kind of exhaustion reaction an athlete is informed by means of a fatigue index. A simple fatigue index is calculated by comparing the sum of AVERAGE-EMG-signals of the main muscle groups used to the exercise in question to the threshold value defined for the athlete in a separate fitness test. When the AVERAGE-EMG sum exceeds the fatigue threshold value a counter is started to measure the time above the threshold. The longer the muscle load of the athlete is above the fatigue threshold the more likely the fatigue of muscles is to cause a reaction hindering the exercise. The accuracy of the fatigue index is better when in calculation is taken into account how high the average load level exceeding the threshold is. This is achieved e.g. by integrating the AVERAGE-EMG sum measured above the fatigue threshold in relation to the time spent above the threshold. Further, the accuracy of the index is improved by combining the results measuring fatigue received from heart rate and R-R interval changes and generated through breathing and blood circulation organs. In addition, changes in motions of the body caused by fatigue as well as information received from external circumstances may be utilized in calculating the index.

In the next advantageous additional application of the invention by means of an EMG-signal an index is calculated to simulate the level of lactate content i.e. level of acidity of blood of a person and changes in the level during exercise. Lactate content is commonly used for describing the level of fatigue of the body and muscles in sports training.

This method of simulating lactate is based on a phenomenon noticed in studies, in which as a result of exertion in the level of an EMG-signal measured from a muscle, nonlinear points may be noticed although external exertion remains constant or the rise is linear. Nonlinear points of an EMG-signal have been noticed to correlate with thresholds of changes of lactate level of the body. Especially this phenomenon may be noticed with so-called anaerobic threshold in which case due to insufficient uptake of oxygen the lactate content begins to accumulate with accelerating speed. Lactate level of the body is typically estimated by measuring the amount of lactate in blood. The normal lactate level in blood at rest and under a light load is typically c. 2 mmol/l. When the load stays on aerobic level, the lactate level may rise to level c. 4 mmol/l, to which stage the body is able to remove lactate by rising the oxygen consumption through breathing. On lactate level 4 mmol/l the body is able to function for a long time without lactate having influence on the function of the body and muscles. On level over 4 mmol/l oxygen uptake is not any more sufficient to remove the extra lactate but its amount begins to accumulate. When exertion continues as it is or rises further the amount of lactate achieves the level where muscles start to stiffen. Therefore, the person has to lower the exertion or to interrupt the exercise to be able to return the amount of lactate to the normal level. This exhaustion level is very individual and it is dependent on the type distribution of muscle fibres, amount of training and methods of training. The ability of the body and muscles to tolerate lactate may be remarkably improved by training.

From an EMG-signal measured during exertion it is possible to calculate in real-time and store in memory e.g. average level of a signal so-called AVERAGE-EMG. An AVERAGE-EMG-signal of muscles acts in an interesting way during fatigue in terms of measurements. When the load on a muscle as fatigue proceeds reaches the level, where all so-called slow-twitch muscle fibres have already been recruited to use with their most powerful activity the muscle has to recruit next so-called fast-twitch muscle fibres. The fibres in question give clearly bigger EMG-response, which means that a rise deviating from the earlier occurs in the EMG-signal level. This moment of rise has been scientifically noticed to take place at the same time as so-called lactate content of blood begins to accumulate.

Lactate content is simulated by means of EMG-measurements such that the value of co-called lactate index is been increased when AVERAGE-EMG-values of muscles exceed the threshold value defined to the person in question and the lactate index is decreased respectively when AVERAGE-EMG-values are below the threshold. The earlier mentioned nonlinear points including changes in signal may be noticed programmatically. When a nonlinear deviation is noticed in EMG-signal level the EMG-level above the threshold is started to be integrated versus time. The criteria of this so-called accumulative integration calculation are defined such that the calculation simulates the amount of lactate accumulating to blood indicating the increasing lactate value. When EMG-signal level falls below the limit value corresponding integration calculation is started which, for its part, simulates the amount of lactate removing from blood. By combining calculations describing earlier mentioned accumulation of lactate and removing of lactate a numerical value is obtained which simulates the amount of lactate in blood in real-time.

In calculation of lactate content additionally also information on heart rate and breathing parameters and changes in those measured simultaneously may be utilized. Especially, in recovering phases included in exercise the lactate level falls depending on how much oxygen the system is able to provide to the most exhausted muscles. For example, a higher respiration rate and bigger volume/minute of breathing (Ventilation) and oxygen consumption (VO2) accelerates the removal of lactate.

In an application in accordance with the invention, also other kinds of indexes may be calculated by utilizing two or more measuring results and by combining them while needed to quantities affecting external circumstances or other quantities affecting the exercise. In this way, it is possible to take into account special features related to different sports and individually to each athlete.

The device in accordance with the invention includes sensors for measuring of other quantities describing exercise than electrical signals of muscles and a means for processing the measuring results and for calculating of one or several indexes describing the exercise.

In an advantageous application of the invention, the device comprises sensors for measuring of other biosignals of a person. In the second advantageous application of the invention, the device comprises sensors for measuring of other movements during exercise and for measuring of their variables and in the third advantageous application of the invention the device comprises sensors for measuring of external circumstances.

In the method in accordance with the invention EMG-signals describing muscle activities are advantageously measured from electrodes placed on muscles to be measured and integrated on an outfit e.g. on shorts, from which electrodes an EMG-signal is conducted to a measuring module for analyzing by means of signal processing electronics and a programme. For measuring the heart rate there are electrodes integrated on the outfit in places from where the EMG-signals needed for measuring may be received. As electrodes and wires are fastened on the outfit there is no need for separate electrodes and wires to be glued on the skin. Due to outfits of the right size and their elastic fabric, the electrodes stay on the right place providing a reliable contact between the electrodes and the skin. For measuring muscle activities and the heart rate also separate sensors to be worn may be used to which the necessary electrodes have been integrated. These kinds of sensors may be placed to measuring points either by fastening the sensor to an outfit covering the place in question or a sensor may be fastened to the body by means of a rubber band, belt, strap or some other suitable means.

When wearing an outfit EMG-electrodes are not always located exactly on a certain muscle and that is not even necessary when wearing an outfit in accordance with the invention, because the main purpose is to compare the total work of muscle groups and limbs and not so much the work of separate muscles.

In an advantageous application of the invention electrodes, conductors made of conductive material and one or several data processing modules for processing measuring results and calculating one or several indexes describing exercises as well as possibly a feedback module have been integrated to an outfit. As electrodes and conductors recognized suitable for the purpose electrodes and conductors are employed. In the application described as an example, textile electrode surfaces and conductors are used but also other kinds of alternatives may be used in other applications. Electrodes, conductors and connections in outfits are washable and wearable.

A means for processing measuring results and for calculating one or several indexes may be placed on the body, on an outfit or an accessory on the body such as a belt, a strap, a wristband or some other accessory or exercise means. A feedback device may correspondingly be placed in recognized way similarly to an outfit, accessory or exercise means. As a feedback device recognized feedback devices are used by means of which the person receives desired information.

In the outfit in accordance with the invention, there are connections to which a module may removably be placed and in the outfit and module, there are equivalent connection parts. In outfits and modules there are standardized connection parts in which case the same module may be used in several outfits. The possibility of changing parts from a worn outfit to a new one allows the long-term use of modules, which reduces costs.

One or several reference (grounding) electrode surfaces have been mounted on an outfit for measuring of EMG. The number and the shape of reference electrodes may vary in accordance with applications. For example, one solid reference surface reduces the number of necessary reference connectors in an outfit and, on the other hand, brings the reference point as close as possible to each muscle/muscle group to be measured. A large reference electrode surface secures a good contact also in motion. On the other hand, by using several separate reference surfaces it is possible, in some cases, to secure a sufficiently good signal from every muscle or muscle group to be measured without interference. Grounding may act while needed also as interference protection for connectors from measuring electrodes.

Acceleration sensors are used for measuring changes in strength of various parts of the body in relation to the direction of motion examined. Acceleration sensors may be either sensors measuring to one direction or integrated sensor components measuring several different directions. The most natural place for an acceleration sensor is the middle part of the body but corresponding information may be distinguished also in case a sensor is placed in other parts of the body. Up/down direction allows most easily calculating the number of steps and the cadence. Sideways the sideway rocking of the body is monitored and the sensor of progression direction tells about changes in speed related to progression. When several acceleration sensors are used one sensor may be placed e.g. on the body and the others on different limbs, in which case the movements of the limbs may be separated from movements of the body and from each other.

A signal describing air pressure is received from a pressure sensor. As air pressure changes in accordance with differences in altitude by analyzing altitude information it is possible to detect whether one is moving on an even terrain or up/down hill. By means of altitude information, it is possible to distinguish from a signal those points in which changes in load are due to some other reason than fatigue in muscles.

The device comprises a location sensor, which is advantageously a GPS-device, with which a person gets information on his/her location.

Next, the invention is described by means of two simplified examples treating running and cycling:

When a healthy athlete in good shape runs on a sports field at a constant speed the total load of his/her leg muscles remains constant (e.g. 1000 uV) for a long time. Only when his/her energy stores are beginning to ebb (e.g. after $t_1$ time), load on muscles starts to grow but the speed of the athlete probably remains unchanged for a while. In case running still continues muscle load grows before long (e.g. in time $t_2$) so high (e.g. 2000 uV) that muscles start to stiffen which causes slowening of speed and at the end exhaustion. By calculating the ratio of running speed and the total load of the muscles an index (MP) is received, which describes the fitness level and economy of running technique of the athlete during various phases of running. At the beginning of the race, the index is big describing good economy but later the index gets smaller as muscle load increases and on the other hand, speed slowens. The better the fitness of the athlete the bigger the index MP (at given speed) and it may therefore utilized as a meter of fitness level/running techniques. This kind of meter, however, gives comparable results only on even running field and under unchanged circumstances.

In case the earlier mentioned runner runs at above mentioned steady speed on a gently climbing slope his/her muscle load is higher than in the situation described earlier because of a greater motion resistance. When running on climbing slope the ratio of speed and the total load of muscles give a smaller index value. Respectively, while running downhill the index value is bigger. This means that the fitness level or the exercise technique may not be estimated by means of MP index because the index includes also load changes caused by various external factors. In case the athlete has a device with him/her measuring changes in terrain profile it is possible to normalize the MP index utilizing those such that the index values are comparable also with measuring results received on an even running field.

In a situation where muscles of the athlete start to become fatigued, the MP index may be used as indicator of fatigue and as a meter of the level of fatigue. As the muscle load increases after time $t_1$ although the speed remains constant, the MP index value starts to change smaller. Especially at the point where in EMG-signal measuring load there is a clear rise the load is on such a critical level, after which the moment of exhaustion $t_2$ is remarkably near. If the athlete continues his/her performance with the same intensity muscles start to stiffen and it is not possible to recover from exhaustion without essentially hindering the exercise or it forces to end the exercise prematurely. The MP index may also be utilized to identify the first symptoms before stiffening begins to happen. As the shape of terrain affects nonlinearly the speed of fatigue, it is possible to specify identification of fatigue made by means of MP index by utilizing changes in terrain profile measured simultaneously. If MP index is noticed to be getting smaller in uphill it is possible to warn the athlete about becoming fatigued earlier than if the same MP index was obtained on even terrain or in downhill.

In cycling, the earlier described MP index calculated from speed and muscle load is possible to be utilized in the same way as in running. There are, however, such variables related to cycling, which do not exist in running. These are, among other things, changing the gear ratio of gears while necessary, free rolling on even terrain and in downhill without muscle load and the possibility to pedal either sitting on a saddle or standing on pedals. It is also possible to remarkably affect loading of muscles by varying technical riding position (e.g. vertical and horizontal adjusting of the saddle and handlebar). In cycling also greater speed differences are obtained between various situations and circumstances, in which case MP index values vary on a larger scale.

MP index may be utilized in cycling training e.g. in optimizing riding techniques for trial on even terrain. In this case, a cyclist rides at even speed with different gearing and compares the MP index values obtained from those. Depending on composition of muscles and riding background of the cyclist, some get the best MP index value with heavy gearing and low pedaling speed and the others respectively with lighter gearings and higher pedaling speeds. It is essential that each cyclist finds himself/herself the most advantageous gearing to suit his/her condition. Respectively, it is also possible to vary the riding position and adjustments of the saddle and handlebar and in that way optimize the efficiency and economy of the exercise. For important competitions, a cyclist may train the effect of the profile of the race track and of presumable weather conditions on the exercise and prepare the competition tactics suitable for himself/herself.

It is possible to define also other parameters measuring fitness level or guiding training for an athlete by means of the earlier mentioned measuring values. For example, in muscle fitness test various kinds of quantities may be identified such as beginning threshold of fatigue, fatigue velocity and exhaustion threshold. The beginning threshold of fatigue may be defined e.g. in a standard muscle fitness test as the moment when the economy of the exercise begins to fall due to fatigue of muscles. Fatigue velocity means the change velocity on AVERAGE-EMG-level in time unit. Exhaustion threshold respectively means the moment when the person to be tested is no more able to maintain the exercise on desired load level and has to lighten essentially the load or even to interrupt the exercise.

Figure 2:
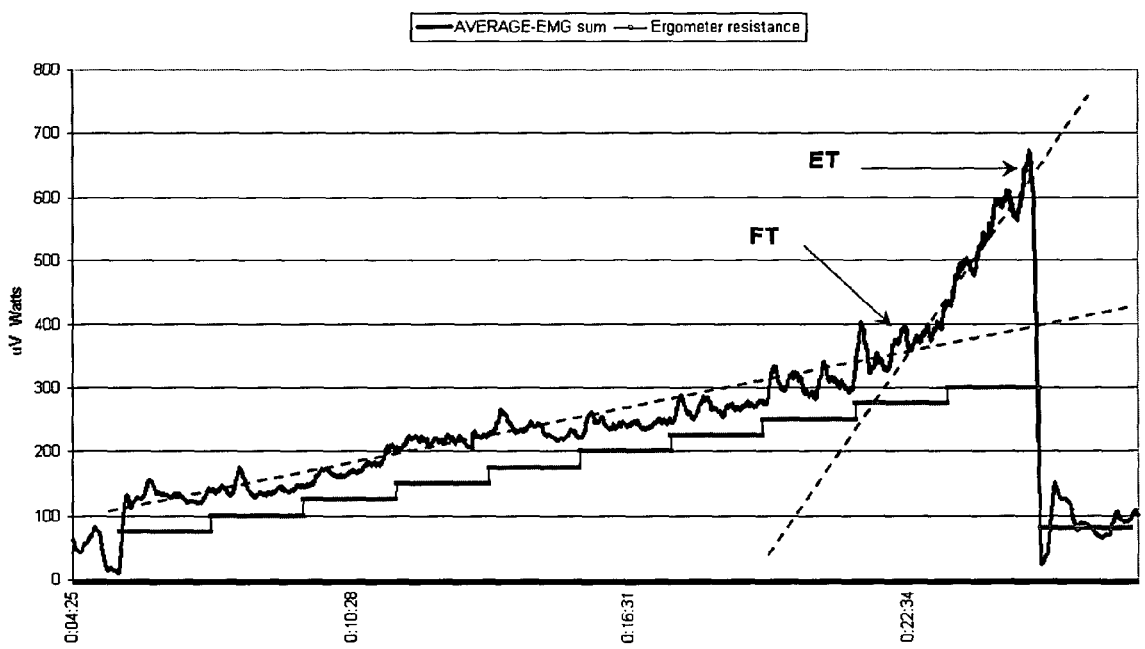

In the next example some parameters describing fitness level and guiding training are treated with reference to the accompanying drawings, in which, FIG. 1 illustrates load curves from a fitness test, and FIG. 2 illustrates quantities to be measured from load curves of muscles in more detail.

FIG. 1 illustrates a fitness test and load curves made on a cycle ergometer. During the fitness test AVERAGE-EMG sum of leg muscles, the heart rate of an athlete and gradually rising ergometer resistance have been measured and stored. It may be seen in figure that the heart rate rises the whole time almost linearly while load grows but in the muscle load curve there is even visible to the eye at least one clear deviation from linearity. Starting from resistance level 275 W the muscle load grows fast and strongly ending with quick exhaustion.

FIG. 2 illustrates some quantities to be measured from a load curve of muscles. By making a simple linear examination seen in the figure it may be noticed that rise differing from linearity of muscle load of the athlete takes place at point 350 µV. This threshold FT corresponds to the load level of the athlete in question at which he/she has to recruit more than usually also so-called fast motor units. It is commonly known that at the same time the lactate content of the athlete begins to accumulate. This happens because the ability of the respiratory and circulatory systems of the athlete to deliver oxygen to muscles is reaching its maximum. This can be noticed from that the heart rate of the athlete is very near to maximum value. As a result of this situation, the muscles of the athlete start to become fatigued. The velocity of fatigue depends on time and changes in load level. In this test, the resistance of ergometer rises automatically to the next level 300 W. The load on muscles of the athlete increases fast in about 2 minutes to the exhaustion level ET i.e. about 650 µV. Fatigue is noticeable especially in that load grows steeply although resistance in itself remains constant.

Level FT is, in this case, the earlier presented beginning threshold of fatigue. The same issue may also be presented by means of economy index MP, which may be defined e.g. as ratio of ergometer resistance and AVERAGE-EMG sum. It is easy to see that the ratio in question remains approximately constant until 275 W but then starts to get smaller as muscle load steeply increases.

From the measured data, also the earlier mentioned fatigue velocity on various load levels may be calculated. Fatigue velocity is dependant on time and changes in load level. In case the resistance of ergometer was in 275 W at the end of the test muscle load would have increased somewhat slower but anyway rather soon to the exhaustion level. In this case, the fatigue velocity on the level in question would be smaller. On the other hand, it seems that during resistance levels lower than 275 W muscle load hardly changes in which case fatigue velocity is ~0.

Individual fatigue threshold FT found in a fitness test may be utilized in guiding of training. In case the resistance of ergometer is set e.g. to 250 W which does not exceed the fatigue threshold FT, fatigue does not occur and the performance may continue without interruptions even for hours. That is called basic endurance training. Interval trainings at 275 W-300 W resistance develop so-called sprint endurance because then the fatigue/recovering properties of muscles improve. The maximum endurance of muscles and systems develops best when the resistance level is minimum 300 W.

By training on threshold level FT and above it especially athlete's lactate tolerance is improved.

As a result of training the exercise capacity of an athlete improves and at the same time threshold levels change. Therefore, a fitness test must be repeated often enough to be able to set the optimal target areas to training.

Things related to exercise capacity and fatigue may also be detected from motion sensors attached on the body. Especially, by means of vertical acceleration it is possible to measure the amplitude of vertical motion of the centre of gravity of a runner. From changes in altitude amplitude the fatigue index IF1 is measured. By the same sensor measuring vertical acceleration also time spent to steps is calculated: Acceleration data is almost periodic and momentary period is the same as the time spent to a step. Measured time intervals of steps form a series of numbers from which the variation of step rhythm and the frequency content of time series at different time are calculated. Further from these, the fatigue index IF2 is calculated. The variation of step rhythm may also be calculated separately for both legs. By measuring variations of sideways acceleration of the centre of gravity of a runner the fatigue index IF3 is obtained. These indexes may be used as such for defining the fatigue level of a runner or they may be combined to fatigue quantities of EMG-measurements to specify a fatigue analysis.

While cycling a sensor of vertical acceleration indicates the riding manner: changes in acceleration while pedaling in standing position are bigger than while riding in sitting position. This information is of great importance in EMG-analysis of cycling. In addition, the amount of work carried out by an athlete may be estimated by means of mentioned measuring results. The amount of work may be proportioned also to correspond to energy consumption during time in question. By combining this information to energy consumption value received by the heart rate it is obtained more accurately and especially energy consumption values from exercises requiring work of big muscles more accurate than only by means of heart rate data would be received.

By measuring all exercises of an athlete by methods in accordance with the invention a cover-all picture on events during training season and progression of training may be obtained. The results give the athlete and the trainer such information, which better than at present may be utilized in following affects of training and also in planning future training programme.

The structure of the outfit in accordance with the invention may vary in various applications of the invention. In different sports different kinds of outfits are used in which case the structure, shape and the location of electrodes are dependent on sports or training event and on which muscle groups are desired to be monitored and examined.

The invention is not limited to the presented advantageous applications but it can vary within the frames of the idea of the invention formed in the claims.

The invention claimed is:

1. A method for measuring exercise level during exercise and for measuring fatigue, in which EMG electrical signals produced by active muscles are measured with a measuring device, besides the EMG electrical signals received from the muscles, a momentary exercise level and a level of fatigue of a person are measured or estimated by also measuring other quantities describing exercise, circumstances and/or environments, wherein the other quantities describing exercise include acceleration, velocity, biomechanical movements or motion paths of a body or limb of the person, or position of the person on an exercise means, wherein the other quantities describing circumstances include weather, temperature, wind, or air pressure, and wherein the other quantities describing environments include resistance due to the exercise means, a setting of the exercise means, altitude or steepness of terrain, from results of the measured EMG electrical signals and from the measuring of the other quantities, one or several indexes are calculated by means of which exercises carried out at different times and under different circumstances and/or environments are comparable with each other, feedback is given from the exercise with a perceivable signal from a feedback device during the exercise, by means of which the person may simultaneously monitor and optimize the exercise.

2. A method in accordance with claim 1, in which in addition other biosignals and/or movements of the person are measured.

3. A method in accordance with claim 1, in which a progression velocity of the person is measured.

4. A method in accordance with claim 1, in which external circumstances are measured.

5. A method in accordance with claim 1, in which from the results an index is calculated for describing an economy of the exercise level and exercise techniques of the person.

6. A method in accordance with claim 1, in which from the results an index is calculated for describing the level of fatigue of the person.

7. A method in accordance with claim 1, in which from the results an index is calculated for simulating a level of lactate content of blood of the person and changes in the level of lactate content during the exercise.

8. A device for measuring exercise level and fatigue during an exercise, comprising:

sensors for measuring EMG electrical signals from active muscles and a feedback device for giving feedback during the exercise, sensors for measuring other quantities describing exercise, circumstances and/or environments, wherein the other quantities describing exercise include acceleration, velocity, changes of biomechanical movements or motion paths of a body or limb of the person or position of the person on an exercise means, wherein the other quantities describing circumstances include weather, temperature, wind, or air pressure, and wherein the other quantities describing environments include resistance due to the exercise means, a setting of the exercise means, altitude or terrain, and means for processing of results from the measured EMG electrical signals and from the other measured quantities and calculating one or several indexes describing exercises.

9. A device in accordance with claim 8, comprising an outfit or similar, in which there are electrodes for measuring electrical biosignals, a module fastened to an outfit, in which there is electronics necessary for processing the biosignals as well as one or several inertia-sensors.

10. A device in accordance with claim 8, comprising sensors for measuring other biosignals of a person.

11. A device in accordance with claim 8, comprising sensors for measuring movements during exercise and variables affecting those.

12. A device in accordance with claim 8, comprising sensors for measuring external circumstances.

13. A device in accordance with claim 8, comprising a speed sensor placed on the body, exercise means or outfit or similar.

14. A device in accordance with claim 8, comprising a tracking sensor comprising a GPS-device.

15. A device in accordance with claim 8, comprising sensors for measuring of one or several external factors such as current of air.

16. A device in accordance with claim 8, comprising a strap or belt to be removably fastened on the body or limbs and which comprises electrodes for measuring electrical biosignals.

* * * * *